(12) United States Patent
Rich

(10) Patent No.: US 7,776,268 B2
(45) Date of Patent: Aug. 17, 2010

(54) USER INTERFACE FOR A FLUIDIC SYSTEM OF A FLOW CYTOMETER

(75) Inventor: Collin A. Rich, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 630 days.

(21) Appl. No.: 11/549,560

(22) Filed: Oct. 13, 2006

(65) Prior Publication Data

US 2009/0104075 A1    Apr. 23, 2009

Related U.S. Application Data

(63) Continuation-in-part of application No. 11/370,714, filed on Mar. 8, 2006.

(60) Provisional application No. 60/727,144, filed on Oct. 13, 2005.

(51) Int. Cl.
  *B01L 3/02* (2006.01)
  *G01N 21/00* (2006.01)
  *G01N 35/02* (2006.01)
  *G01N 15/02* (2006.01)
  *G01N 15/06* (2006.01)

(52) U.S. Cl. ............... 422/81; 422/62; 422/67; 422/68.1; 422/73; 422/100; 422/101; 436/50; 436/52; 356/335; 356/336; 356/337; 356/338

(58) Field of Classification Search ............ None
See application file for complete search history.

(56) References Cited

U.S. PATENT DOCUMENTS

| | | | |
|---|---|---|---|
| 3,672,402 A | 6/1972 | Bloemer | |
| 4,112,735 A | 9/1978 | McKnight | |
| 4,138,879 A | 2/1979 | Liebermann | |
| 4,371,786 A | 2/1983 | Kramer | |
| 4,448,538 A | 5/1984 | Mantel | |
| 4,559,454 A | 12/1985 | Kramer | |
| 4,790,653 A | 12/1988 | North, Jr. | |
| 4,818,103 A | 4/1989 | Thomas et al. | |
| 4,844,610 A | 7/1989 | North, Jr. | |
| 5,040,890 A | 8/1991 | North, Jr. | |
| 5,043,706 A | 8/1991 | Oliver | |
| 5,083,862 A | 1/1992 | Rusnak | |
| 5,155,543 A | 10/1992 | Hirako | |
| 5,395,588 A | 3/1995 | North, Jr. | |

(Continued)

FOREIGN PATENT DOCUMENTS

EP    1521076    9/2004

(Continued)

*Primary Examiner*—Jill Warden
*Assistant Examiner*—Neil Turk
(74) *Attorney, Agent, or Firm*—Jeffrey Schox

(57) ABSTRACT

The fluidic system of the preferred embodiment includes a sheath pump to pump sheath fluid from a sheath container into an interrogation zone and a waste pump to pump waste fluid from the interrogation zone into a waste container. The sheath pump and/or the waste pump draw sample fluid from a sample container into the interrogation zone. The fluidic system also includes a controller to adjust the flow rate of the sample fluid from the sample container into the interrogation zone. The fluidic system is preferably incorporated into a flow cytometer with a flow cell that includes the interrogation zone.

12 Claims, 2 Drawing Sheets

U.S. PATENT DOCUMENTS

| | | | |
|---|---|---|---|
| 5,403,552 A * | 4/1995 | Pardikes | 422/62 |
| 5,539,386 A | 7/1996 | Elliot | |
| 5,552,885 A | 9/1996 | Steen | |
| 6,039,078 A | 3/2000 | Tamari | |
| 6,110,427 A | 8/2000 | Uffenheimer | |
| 6,156,208 A | 12/2000 | Desjardins et al. | |
| 6,183,697 B1 | 2/2001 | Tanaka | |
| 6,288,783 B1 | 9/2001 | Auad | |
| 6,382,228 B1 | 5/2002 | Cabuz | |
| 6,427,521 B2 | 8/2002 | Jakkula et al. | |
| 6,568,271 B2 | 5/2003 | Shah et al. | |
| 6,602,469 B1 * | 8/2003 | Maus et al. | 422/68.1 |
| 6,694,799 B2 | 2/2004 | Small | |
| 6,825,926 B2 | 11/2004 | Turner | |
| 6,852,284 B1 | 2/2005 | Holl et al. | |
| 6,872,180 B2 | 3/2005 | Reinhardt et al. | |
| 6,908,226 B2 | 6/2005 | Siddiqui et al. | |
| 6,912,904 B2 | 7/2005 | Storm, Jr. et al. | |
| 6,941,005 B2 | 9/2005 | Lary et al. | |
| 7,019,834 B2 | 3/2006 | Sebok et al. | |
| 7,061,595 B2 | 6/2006 | Cabuz | |
| 2002/0028434 A1 | 3/2002 | Goix | |
| 2002/0059959 A1 | 5/2002 | Qatu et al. | |
| 2002/0123154 A1 | 9/2002 | Burshteyn | |
| 2003/0054558 A1 | 3/2003 | Kurabayashi | |
| 2003/0062314 A1 | 4/2003 | Davidson et al. | |
| 2003/0072549 A1 | 4/2003 | Facer et al. | |
| 2003/0129090 A1 * | 7/2003 | Farrell | 422/68.1 |
| 2003/0202175 A1 | 10/2003 | Van den Engh et al. | |
| 2003/0211009 A1 | 11/2003 | Buchanan | |
| 2003/0223061 A1 | 12/2003 | Sebok et al. | |
| 2004/0031521 A1 | 2/2004 | Vrane et al. | |
| 2004/0112808 A1 | 6/2004 | Takagi et al. | |
| 2004/0123645 A1 | 7/2004 | Storm, Jr. et al. | |
| 2005/0069454 A1 | 3/2005 | Bell | |
| 2005/0195684 A1 | 9/2005 | Mayer | |
| 2005/0252574 A1 | 11/2005 | Khan et al. | |
| 2006/0286549 A1 | 12/2006 | Sohn | |
| 2007/0003434 A1 | 1/2007 | Padmanabhan | |

FOREIGN PATENT DOCUMENTS

| | | |
|---|---|---|
| EP | 1521076 | 4/2005 |
| WO | WO/2005/017499 | 2/2005 |
| WO | 2005017499 | 8/2005 |

\* cited by examiner

US 7,776,268 B2

USER INTERFACE FOR A FLUIDIC SYSTEM OF A FLOW CYTOMETER

CROSS-REFERENCE TO RELATED APPLICATIONS

This application is a continuation-in-part of prior application Ser. No. 11/370,714 filed 8 Mar. 2006 and entitled "Fluidic System for a Flow Cytometer", which is incorporated in its entirety by this reference. This application also claims the benefit of U.S. Provisional Application No. 60/727,144 filed on 13 Oct. 2005 and entitled "Core Stream Controller", which is incorporated in its entirety by this reference.

TECHNICAL FIELD

This invention relates generally to the flow cytometer field, and more specifically to an improved fluidic system in the flow cytometer field.

BACKGROUND

In typical flow cytometry systems, the fluidics system functions to draw sample particles into a sample stream and transport the sample stream through an interrogation zone. The fluidics system typically uses a pressurized sheath stream to hydrodynamically focus the sample stream, which is known as the core stream, within the center of the sheath stream. The process of hydrodynamic focusing (also known as coaxial flow) results in laminar flow under preferred conditions and enables the optical system of the flow cytometer to illuminate, and thus analyze, the sample particles with uniformity and repeatability. Ideally, the particles within the core stream are positioned in the center of the interrogation zone and are arranged in a "single file" line. To accomplish this particle arrangement across multiple sample particle sizes, the core stream is adjusted in an open loop manner by multiple controls that alter (1) the pressure of the sample line, (2) the pressure of the sheath line, and (3) the sample-to-sheath pressure differential. Most commonly, at least two of the three settings will need to be adjusted in the course of setting the core stream size.

Adjusting the multitude of controls used to set the core stream, including the sample flow rate (i.e. sample line pressure), sheath flow rate (i.e. sheath line pressure), and sample-to-sheath pressure differential often requires multiple iterations of adjustments. Setting the multiple control flow cytometer core stream controls can be challenging to, and time consuming for, the experienced user, and can lead to inaccurate data (i.e. event) collection and suboptimal core stream formation in the hands of an inexperienced user. Furthermore, a substantial amount of sample must be consumed in order to set the pressure settings, which is a further disadvantage of the present system particularly when the sample to be analyzed is available in a very limited quantity.

Thus, there is a need in the flow cytometer field to create a new, improved, and useful fluidic system that avoids or minimizes these disadvantages. This invention provides such a new, improved, and useful fluidic system for a flow cytometer.

DESCRIPTION OF THE PREFERRED EMBODIMENT

The following description of the preferred embodiment of the invention is not intended to limit the invention to this preferred embodiment, but rather to enable any person skilled in the art of flow cytometers to make and use this invention.

Figure 1:
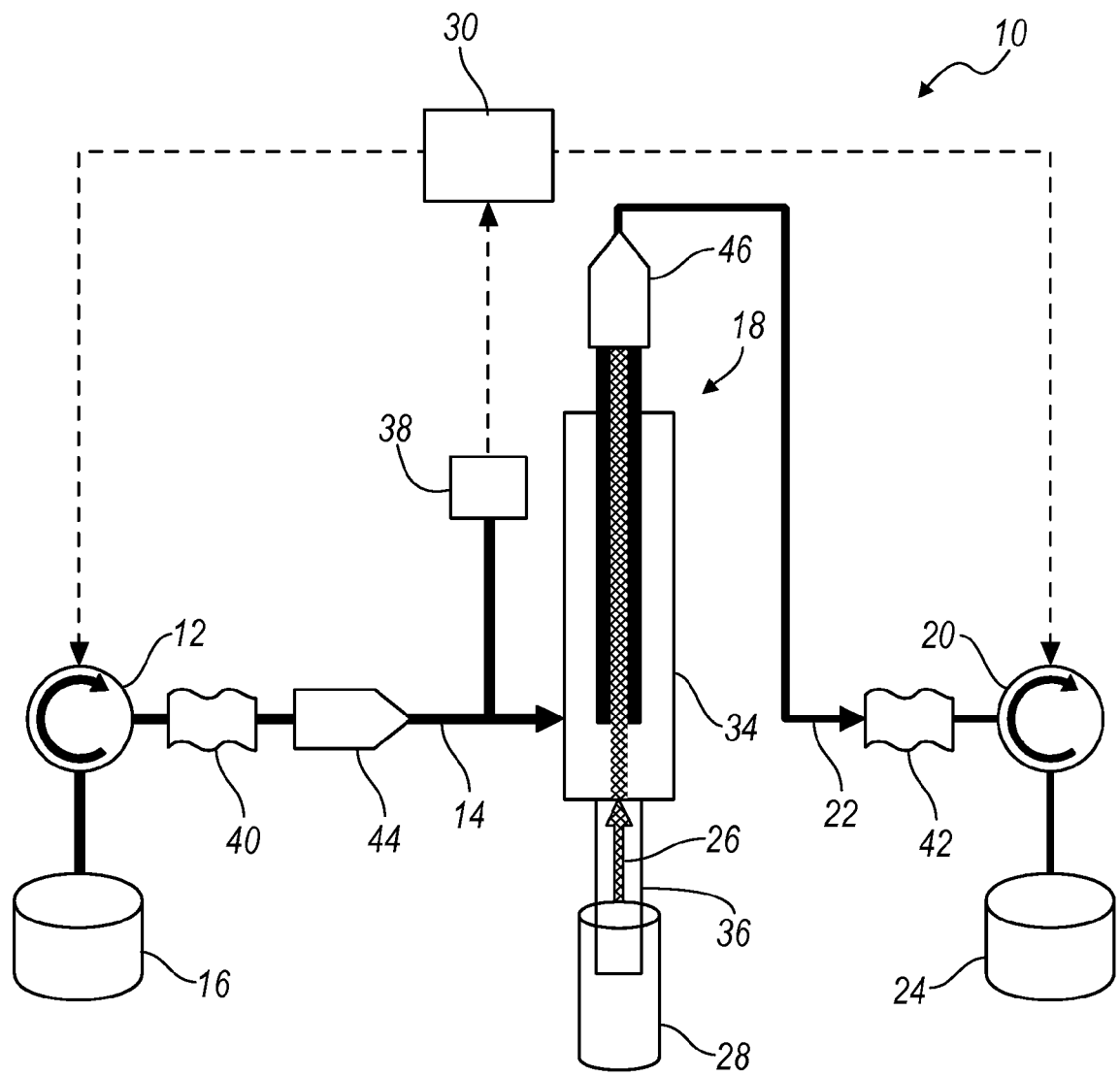
FIG. 1 is a schematic representation of the fluidic system of the preferred embodiment of the invention.
Figure 2:
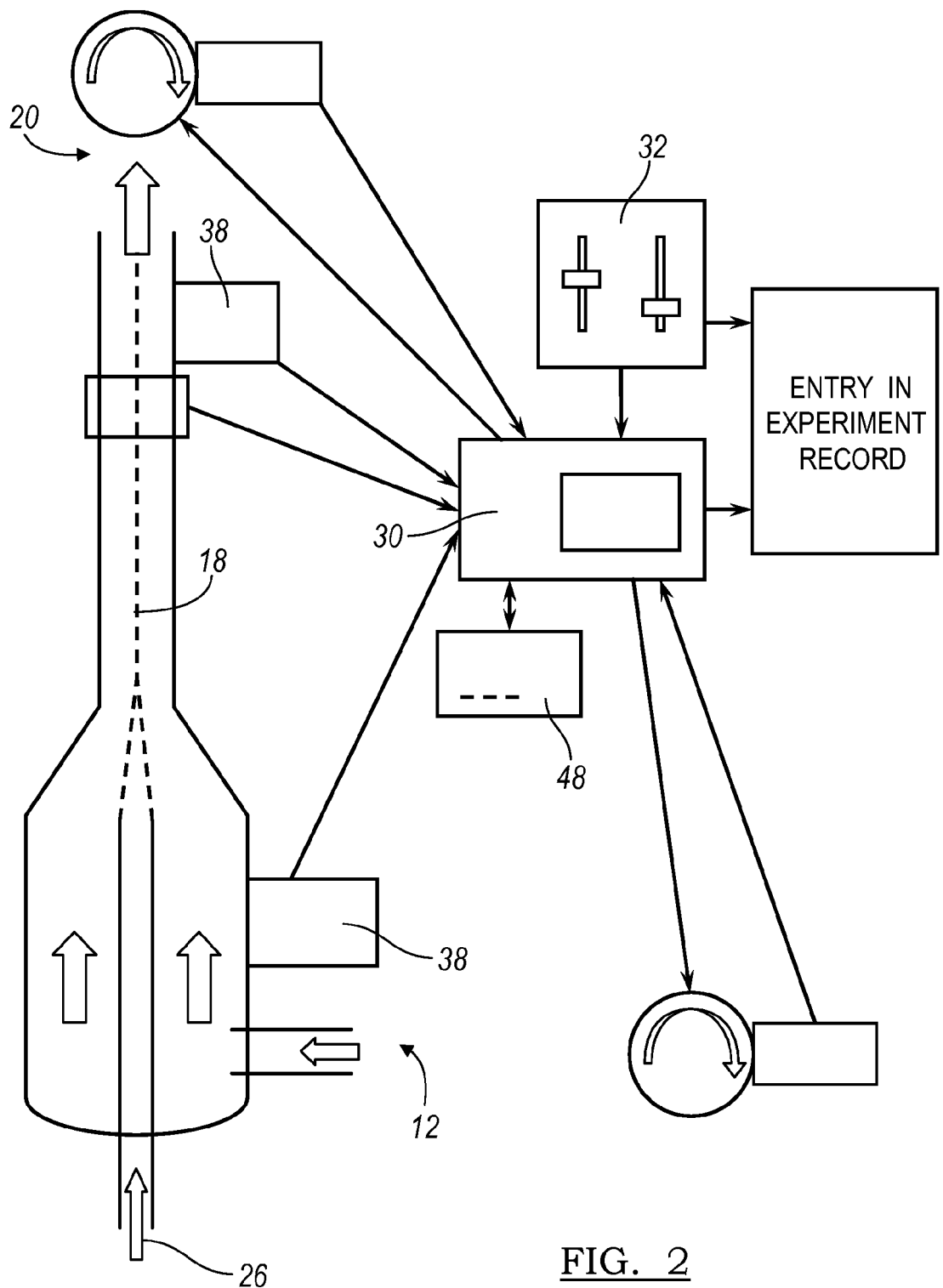
FIG. 2 is a schematic representation of the user interface of the preferred embodiment of the invention

As shown in FIGS. 1 and 2, the fluidic system 10 of the preferred embodiment includes a sheath pump 12 to pump sheath fluid 14 from a sheath container 16 into an interrogation zone 18 and a waste pump 20 to pump the sheath fluid 14 and a sample fluid 26 as waste fluid 22 from the interrogation zone 18 into a waste container 24. The sheath pump 12 and/or the waste pump 20 draw sample fluid 26 from a sample container 28 into the interrogation zone 18. The fluidic system 10 also includes a controller 30 to adjust the flow rate of the sample fluid 26 from the sample container 28 into the interrogation zone 18. The fluidic system 10 also includes a user interface 32 to receive an input from a user. The interrogation zone 18 functions to provide a location for the fluidic system 10 and an optical system of the flow cytometer to cooperatively facilitate the analysis of the sample fluid 26. The interrogation zone 18 is preferably enclosed within a removable flow cell 34, but may alternatively be defined by any suitable system or device. The fluidic system 10 is preferably incorporated into a flow cytometer, but may be alternatively incorporated into any suitable system that pumps a first fluid from a first container into an interrogation zone 18, draws a second fluid from a second container into the interrogation zone 18, and pumps the combined fluids from the interrogation zone 18 into a third container.

As shown in FIG. 1, the sheath pump 12 of the preferred embodiment functions to pump sheath fluid 14 from a sheath container 16 into an interrogation zone 18. The sheath fluid 14 functions to hydrodynamically focus the sample fluid 26. The process of hydrodynamic focusing results in laminar flow of the sample fluid 26 within the flow cell 34 and enables the optical system to illuminate, and thus analyze, the particles within the sample fluid 26 with uniformity and repeatability. Preferably, the sheath fluid 14 is buffered saline or de-ionized water, but the sheath fluid 14 may alternatively be any suitable fluid to hydrodynamically focus the sample fluid 26. The sheath container 16 functions to contain the sheath fluid 14. The sheath container 16 is preferably a vented tank with a volume of approximately 1 L, but the sheath tank may alternatively be any suitable container to contain the sheath fluid 14. Preferably, the sheath pump 12 is a positive displacement pump. More preferably, the sheath pump 12 is a peristaltic pump with a flexible tube and one or more cams that pump the sheath fluid 14 through the flexible tube. The sheath pump 12 preferably has a known flow rate to pump speed ratio, such that control of the speed of the sheath pump 12 corresponds to a control of the flow rate of the sheath fluid 14. With this pump type, the fluidic system 10 is relatively easy to assemble, light to haul, quick to control, and easy to clean. Alternatively, the sheath pump 12 may be any suitable pump that pumps sheath fluid 14 from a sheath container 16 into an interrogation zone 18.

The waste pump 20 of the preferred embodiment functions to pump the waste fluid 22 from the interrogation zone 18 into a waste container 24. Preferably, the waste fluid 22 includes the sheath fluid 14 and the sample fluid 26. Alternatively, the waste fluid 22 may include any fluid that exits the interrogation zone 18. The waste container 24 is preferably a vented tank with a volume of approximately 1 L, but the waste tank may alternatively be any suitable container to contain the waste fluid 22. Like the sheath pump 12, the waste pump 20 is preferably a positive displacement pump and more preferably a peristaltic pump with a flexible tube and one or more cams that pump the waste fluid 22 through the flexible tube. The waste pump 20 preferably has a known flow rate to pump speed ratio, such that control of the speed of the waste pump 20 corresponds to a control of the flow rate of the waste fluid 22. With this pump type, the fluidic system 10 is relatively easy to assemble, light to haul, quick to control, and easy to clean. Alternatively, the waste pump 20 may be any suitable pump that pumps waste fluid 22 from a waste container 24 into an interrogation zone 18.

The sheath pump 12 and the waste pump 20 of the preferred embodiment cooperate to draw the sample fluid 26 from the sample container 28 and through a drawtube 36. The sample fluid 26 contains particles to be analyzed by the flow cytometer. The sample fluid 26 is preferably blood, but the sample fluid 26 may alternatively be any suitable fluid to be analyzed by the flow cytometer. The sample container 28, which functions to contain the sample fluid 26, is preferably an open beaker with a volume of approximately 5 mL, but may alternatively be any suitable container to contain the sample fluid 26. The drawtube 36, functions to convey the sample fluid 26 from the sample container 28 into the interrogation zone 18, is a conventional drawtube, but may alternatively be any suitable device to convey the sample fluid 26.

The sheath pump 12 and the waste pump 20 preferably cooperate to draw the sample fluid 26 from the sample container 28 into the interrogation zone 18 through the use of a pressure differential (e.g., the sheath pump 12 "pushes" the sheath fluid 14 and the waste pump 20 "pulls" the sheath fluid 14 and the sample fluid 26). In order to allow a variable flow rate of the sample fluid 26, the fluidic system 10 preferably allows for a variable flow rate of the sheath fluid 14 and/or the waste fluid 22. In a first variation, the sheath pump 12 and the waste pump 20 are driven by a single motor, but with a variable drive ratio device (e.g., transmission), such that the sheath pump 12 and the waste pump 20 may be operated at different pump speeds and, therefore, allow for a variable flow rate of the sheath fluid 14 and/or the waste fluid 22. In a second variation, the sheath pump 12 and the waste pump 20 are driven by a single motor, but the fluidic system 10 includes at least one by-pass valve located near the sheath pump 12 and/or the waste pump 20. The by-pass valve diverts a variable amount of the fluid flow and, therefore, allows for a variable flow rate of the sheath fluid 14 and/or waste fluid 22. In a third variation, the sheath pump 12 and the waste pump 20 are driven by a single motor, but the fluidic system 10 includes at least one restrictive valve located near the sheath pump 12 and/or the waste pump 20. The restrictive valve alters the fluid flow and, therefore, allows for a variable flow rate of the sheath fluid 14 and/or waste fluid 22. In a fourth variation, the sheath pump 12 and the waste pump 20 are driven by separate motors with separate controls and, therefore, allows for a variable flow rate of the sheath fluid 14 and/or waste fluid 22. The fluidic system 10 may, however, include other suitable variations that draw the sample fluid 26 from the sample container 28 into the interrogation zone 18 through the use of a pressure differential.

The controller 30 of the preferred embodiment functions to adjust the flow rate of the sample fluid 26 from the sample container 28 into the interrogation zone 18. Preferably, the controller 30 adjusts the flow rate of the sample fluid 26 by adjusting the variable flow rate of the sheath fluid 14 and/or the waste fluid 22. More preferably, the controller 30 adjusts the flow rate of the sample fluid 26 by allowing an adjustable flow rate of the sheath fluid 14 from the sheath container 16 to the interrogation zone 18, while maintaining a consistent flow rate of the waste fluid 22 from the interrogation zone 18 into the waste container 24. The advantage of this arrangement is a finer control. of the flow rate of the sample fluid 26. Alternatively, the controller 30 may adjust the flow rate of waste fluid 22 while maintaining the flow rate of the sheath fluid 14, or may simultaneously adjust the flow rates of the sheath fluid 14 and the waste fluid 22. Furthermore, the controller 30 may employ one technique (such as allowing an adjustable flow rate of the sheath fluid 14, while maintaining a consistent flow rate of the waste fluid 22) in most situations, and may employ another technique (such as simultaneously adjusting the flow rates of the sheath fluid 14 and the waste fluid 22) in other situations to quickly response to a user input. The controller 30 is preferably a proportional-integral-derivative (PID) controller, but may alternatively be a proportional-integral (PI) controller, a proportional-derivative (PD) controller, a proportional (P) controller, or any other suitable controller.

As shown in FIG. 2, the fluidic system 10 of the preferred embodiment also includes a user interface 32 that facilitates the receipt of an input from a user that controls the controller 30 (also called a core stream controller). The user interface 32 is connected to the controller 30 and functions to allow adjustment of the flow rate of the sample fluid 26 from the sample container 28 into the interrogation zone 18. The input from the user is preferably a single adjustment, or a more intuitive input from the user, and preferably is at least one of following three parameters: a desired core stream diameter, a core stream fluid type, and an estimated sample particle size. Preferably, the user interface 32 is internally based on flow rates of the sheath fluid and/or the waste fluid, but externally based on one of above three parameter. In contrast to conventional flow cytometry systems, the user sets the flow rate of the sample fluid based on intuitive controls, rather than the sample stream flow rate/pressure, sheath stream flow rate/pressure, and/or sample-to-sheath pressure differential, in order to achieve near-optimal flow.

In a first variation, the controller 30 preferably accesses a lookup table to correlate the input from the user to the flow rate of the sample fluid. The lookup table preferably includes data based on previous sample runs of the flow cytometer, based on sample runs by users of different—yet comparable—flow cytometers (e.g. researchers studying at a remote R&D facility), and/or based on empirical data conducted and developed by the manufacturer or developer of the flow cytometer system. The stored information preferably includes the type of the core stream fluid, the identification of the sample particle, and flow rate of the sample fluid, but may alternatively include any suitable information. The controller 30 may also be further adapted to access the lookup table via a computer network.

In a second variation, the controller 30 preferably includes a storage device 48 with accessible memory. The user interface 32 and accessible memory permit the user to access stored information about similar sample runs and the system configuration and settings that were utilized during those runs. The stored information preferably includes the date of the sample run, the type of the core stream fluid, the identification of the sample particle, and flow rate of the sample fluid, identification of the user, the date of the sample run, exemplary data, and comments from the user, but may alternatively include any suitable information. This stored information can be accessed by the user and retrieved by the controller 30 and flow cytometry system. The user can then, by simply interfacing with the controller 30, automatically set up the pressures and/or flow rates of the sample, sheath, and/or waste streams utilizing those previous sample run settings. Furthermore, once the user has completed a sample run, they can save the controller settings and use the saved information for future sample runs. In a variation of this embodiment, the accessible memory in the flow cytometry system is capable of retrieving remotely saved information about sample runs on similar flow cytometer systems and sample types via a computer network.

Examples of sample run information suitable for later use include: user identification and contact information; date of sample run; identification of the flow cytometer system; identification of the type of flow cytometry analyses conducted (e.g. sorting based on a given wavelength, sample particle counting); type of sample analyzed (e.g. mammalian fibroblast cells, FITC-labeled leukocytes, BODIPY-conjugated proteins, etc.); type of sheath fluid used (e.g. phosphate buffered saline, air); exemplary data from the run (e.g. screen shots, text, or graph files); notes intended for future reference (e.g. problems, suggestions); and, of course, pressure and/or flow rates associated with the sample, sheath, and/or waste streams. Previous sample run information can be stored and accessed by any suitable means from any suitable location or device. Examples of how run information could be saved and accessed include: file name, date of sample run, or type of sample to be analyzed. Sample run data may be stored on a computer component within the flow cytometer system, on a computer network, or in any other suitable location or system.

In another variation, the flow cytometry system of the preferred embodiment includes a core stream detector connected to, and in communication with, the controller 30 to achieve an optimum core stream. The core stream detector functions to identify basic core stream characteristics and transmits the information to the controller 30. Based on this information, the controller 30 dynamically alters the pressures and/or flow rates of the sample, sheath, and/or waste streams in order to approach an optimal core stream. Thus, the core stream detector and the information act as a feedback loop. The core stream detector preferably detects any suitable core stream characteristics. Examples of characteristics include the actual core stream diameter, time elapsed between the passage of sample particles through the interrogation zone, and flow rate of sample particles through the interrogation zone. The core stream detector is preferably located nearby the interrogation zone 18, but may be alternatively located in any suitable location and physically combined with other components of the flow cytometer system. For example, the core stream detector may alternatively be connected to a processor and may receive and transmit information about the acquired data, such as the coefficient variation of the acquired data. In addition, the controller 30 may receive information about other characteristics affecting the core stream from the optical components of the flow cytometry system, such as the time of flight of the sample particles and the number of particles per second that pass through the interrogation zone. The flow cytometer system and/or the controller 30 may dynamically change the parameters of the sample, sheath, and/or waste lines during the analysis of a sample to maintain a particular sample particle velocity, sample fluid flow rate, coefficient variation of the acquired data, or any other suitable parameter. This dynamic change could be predetermined (e.g., to incorporate different parameter settings for different trials), or could be based on an appropriate feedback.

In yet another variation, the flow cytometry system of the preferred embodiment includes a core stream detector connected to, and in communication with, a processor. Like the above variation, this core stream detector functions to identify basic core stream characteristics and transmit this information. Unlike the above variation, however, this information is used to electronically compensate and adjust the acquired data to achieve consistent data.

As shown in FIG. 1, the fluidic system 10 of the preferred embodiment also includes a pressure sensor 38 that functions to measure a pressure of the sheath fluid 14 as close as possible to the inlet for the sample fluid 26. This measured pressure is an adequate estimate for the pressure of the sample fluid 26. The pressure sensor 38 preferably measures a pressure differential between the top of the drawtube 36 near the flow cell 34 and the bottom of the drawtube 36 near the sample container 28, but may alternatively measure a pressure differential between the drawtube 36 and atmosphere. The controller 30 is preferably connected to the pressure sensor 38 and adjusts the flow rate of the sample fluid 26 based on the measured pressure. The controller 30 may alternatively or additionally be connected to other suitable devices to assist in the control of the flow rate of the sample fluid 26. In a first variation, the fluidic system 10 may include a flow meter that functions to measure the flow rate of the sample fluid 26 from the sample container 28 into the interrogation zone 18. In a second variation, the fluidic system 10 may include an input device that functions to receive information related to a fluidic resistance of a drawtube 36 that transports the sample fluid 26 from the sample container 28 into the interrogation zone 18. The input device is preferably an optical device (e.g., a bar code scanner) or an electromagnetic device (e.g., a RFID receiver) that functions to automatically scan and read a code on the drawtube 36. The code is preferably cross-referenced with empirically derived information regarding the fluidic resistance of the drawtube 36. The input device may alternatively be a user-interface device that accepts a code or value related to the fluidic resistance of the drawtube 36. In a third variation, the fluidic system 10 may be substantially self-calibrating according to the following steps: the user places a drawtube 36 of the flow cell 34 into a known fluid (such as buffered saline), the user pumps waste fluid 22 from the interrogation zone 18 into a waste container 24 while maintaining a negligible flow rate of the sheath fluid 14 thereby drawing the known fluid through the drawtube 36 and into the interrogation zone 18, and the fluidic system 10 (through measurement of the flow rate of the waste fluid 22 or any other suitable parameter) estimates the resistance of the drawtube 36. With this estimated resistance of the drawtube 36 for the flow cell 34 combined with the measured pressure of the sheath fluid 14, the controller 30 adjusts the flow rate of the sample fluid 26 with greater accuracy and control.

The fluidic system 10 of the preferred embodiment also includes a first fluidic capacitor 40 located between the sheath container 16 and the interrogation zone 18 and a second fluidic capacitor 42 located between the interrogation zone 18 and the waste container 24. The fluidic capacitors 40 and 42 function to attenuate pulsations within the fluidic system 10. More specifically, the first fluidic capacitor 40 functions to temporarily expand/contract to thereby accumulate/release the sheath fluid 14 and attenuate pulsations within the sheath fluid 14. Similarly, the second fluidic capacitor 42 functions to temporarily expand/contract to thereby accumulate/release the waste fluid 22 and attenuate pulsations within the waste fluid 22. The fluidic capacitors 40 and 42 are selected from the group consisting of bellows-type with a diaphragm, bellows-type without a diaphragm, captive ball-type, and flexible tube-type. The fluidic capacitors 40 and 42 are preferably similar to the fluidic attenuators described in U.S. patent application Ser. No. 11/297,667 entitled "Pulsation Attenuator For A Fluidic System" and filed 7 Dec. 2005, which is hereby incorporated in its entirety by this reference. The fluidic capacitors 40 and 42 may, however, be any suitable device to attenuate pulsations within the fluidic system 10.

The fluidic system 10 of the preferred embodiment also includes a valve 44 located between the first fluidic capacitor and the interrogation zone 18, and a valve 46 located between the interrogation zone 18 and the second fluidic capacitor. The valves 44 and 46 function to facilitate the control of the sheath fluid 14 and the waste fluid 22. The valves 44 and 46 are preferably check-valves, but may alternatively be any suitable valve to facilitate the control of the sheath fluid 14 and the waste fluid 22.

The fluidic system 10 of the preferred embodiment is preferably operated with the following steps: (1) pumping sheath fluid 14 from a sheath container 16 into an interrogation zone 18 and pumping the sheath fluid 14 and the sample fluid 26 as waste fluid 22 from the interrogation zone 18 into a waste container 24, thereby drawing sample fluid 26 from a sample container 28 into the interrogation zone 18; and (2) adjusting the flow rate of the sample fluid 26 from the sample container 28 into the interrogation zone 18. As explained above, step (2) preferably includes allowing a substantially adjustable flow rate of the sheath fluid 14 from the sheath container 16 to the interrogation zone 18, while maintaining a substantially consistent flow rate of the waste fluid 22 from the interrogation zone 18 into the waste container 24. The operation of the fluidic system 10 also preferably includes attenuating pulsations within the sheath fluid 14 and the waste fluid 22.

As a person skilled in the art of flow cytometers will recognize from the previous detailed description and from the figures and claims, modifications and changes can be made to the preferred embodiment of the invention without departing from the scope of this invention defined in the following claims.

I claim:

1. A fluidic system for pumping sheath fluid and sample fluid into an interrogation zone of a flow cytometer, comprising:
    a sheath pump that pumps sheath fluid from a sheath container into an interrogation zone;
    a waste pump that pumps waste fluid from the interrogation zone into a waste container;
    a drawtube, coupled to the sample container, that conveys the sample fluid from the sample container to the interrogation zone;
    wherein the sheath pump and the waste pump cooperate to draw sample fluid from a sample container through the drawtube into the interrogation zone;
    a user interface that receives, from a user, an input selected from the group consisting of: desired core stream diameter, core stream fluid type, and estimated sample particle size;
    a pressure sensor that measures a pressure differential of the sample fluid between the top of the drawtube and the bottom of the drawtube; and
    a controller coupled to the user interface and to the pressure sensor, wherein the controller is configured to adjust the flow rate of the sample fluid from the sample container through the drawtube into the interrogation zone, based on the user input and the measured pressure differential.

2. The fluidic system of claim 1, further including a storage device coupled to the user interface, wherein the user interface receives and the storage device stores information related to previous sample runs, wherein the stored information includes the type of the core stream fluid, the identification of the sample particle, and flow rate of the sample fluid.

3. The fluidic system of claim 2, wherein the user interface receives and the storage device stores information related to the identification of the user, the date of the sample run, and exemplary data.

4. The fluidic system of claim 3, wherein the user interface receives and the storage device stores information related to comments from the user.

5. The fluidic system of claim 1, further including a core stream detector coupled to the controller that identifies core stream characteristics selected from the group consisting of the actual core stream diameter and time elapsed between the passage of sample particles through the interrogation zone, wherein the controller controls at least one of the flow rates of the sheath fluid and the waste fluid based on the input from the user and the identified core stream characteristics.

6. The fluidic system of claim 1, wherein the controller adjusts the flow rate of the sample fluid by allowing an adjustable flow rate of the sheath fluid pumped from the sheath container to the interrogation zone.

7. The fluidic system of claim 6, wherein the controller adjusts the flow rate of the sample fluid by maintaining a consistent flow rate of the waste fluid pumped from the interrogation zone into the waste container.

8. The fluidic system of claim 7, wherein the controller is a proportional-integral-derivative controller (PID controller), wherein the controller includes a storage device coupled to the user interface, wherein the user interface receives and the storage device stores information related to previous sample runs.

9. The fluidic system of claim 1, further including a core stream detector coupled to the controller that identifies core stream characteristics, wherein the controller controls at least one of the flow rates of the sheath fluid and the waste fluid further based on the input from the user and the identified core stream characteristics.

10. The fluidic system of claim 9, wherein the core stream characteristics are selected from the group consisting of the actual core stream diameter, time elapsed between the passage of sample particles through the interrogation zone, and flow rate of sample particles through the interrogation zone.

11. The fluidic system of claim 1, further comprising a storage device coupled to the user interface, wherein the user interface receives and the storage device stores information related to previous sample runs, wherein the stored information includes the type of the core stream fluid, the identification of the sample particle, and flow rate of the sample fluid.

12. The fluidic system of claim 11, wherein the user interface receives and the storage device stores information related to the identification of the user, the date of the sample run, exemplary data, and comments from the user.

* * * * *